(12) United States Patent
Wardlaw

(10) Patent No.: US 6,262,799 B1
(45) Date of Patent: Jul. 17, 2001

(54) METHOD AND APPARATUS FOR RAPID MEASUREMENT OF CELL LAYERS

(75) Inventor: Stephen C. Wardlaw, Lyme, CT (US)

(73) Assignee: Robert A. Levine, Guilford, CT (US)

(*) Notice: Subject to any disclaimer, the term of this patent is extended or adjusted under 35 U.S.C. 154(b) by 0 days.

(21) Appl. No.: 09/338,042

(22) Filed: Jun. 22, 1999

(51) Int. Cl.[7] .................................................... G01N 33/48

(52) U.S. Cl. .................................. 356/39; 356/40; 356/42

(58) Field of Search .................................. 356/39, 40, 42

(56) References Cited

FOREIGN PATENT DOCUMENTS 41 16 313 A1   11/1992   (DE) .

*Primary Examiner*—Frank G. Font
*Assistant Examiner*—Reginald A. Ratliff
(74) *Attorney, Agent, or Firm*—William W. Jones

(57) ABSTRACT

Centrifuged material layer volumes are measured and quantified during centrifugation of the material layers. The material layers are differentially highlighted by means of one or more supravital fluorescent dyes or stains which are admixed with the sample being analyzed. This kinetic quantification procedure is particularly useful in performing differential blood cell and platelet counts. The blood sample is centrifuged while being subjected to an intense filtered strobed light source at two different wavelengths. At least one photometric cell layer compaction measurement is made in conjunction with the light flashes so as to record a degree of cell layer compaction as the sample is being centrifuged. In certain cases, after several successive cell layer compaction readings are derived, a compaction curve is identified and the ultimate degree of cell layer compaction is calculated from the derived compaction curve prior to the achievement of the ultimate degree of cell layer compaction.

2 Claims, 4 Drawing Sheets

METHOD AND APPARATUS FOR RAPID MEASUREMENT OF CELL LAYERS

TECHNICAL FIELD

This invention relates to a method for rapidly making centrifuged material layer volume measurements. The method of this invention is particularly useful in performing blood constituent count measurements in a centrifuged sample of anticoagulated whole blood while the blood sample is being centrifuged.

BACKGROUND ART

The measurement of the blood cell counts in a centrifuged sample of anticoagulated whole blood has been described in the scientific literature, and a method for easily measuring certain blood cell and other constituent layers is described in U.S. Pat. No. 4,027,660, granted Jun. 7, 1977 to Stephen C. Wardlaw et al. In the patented method, a sample of anticoagulated whole blood is centrifuged in a precision capillary tube which contains a plastic float. The float linearly expands some of the cell layers and the platelet layer.

In performing the patented method, the blood sample is centrifuged for about five minutes at about 12,000 RPM, and then the expanded lengths of the cell and platelet layers are measured. One of the problems in the patented method pertains to the need for the operator to remove the tube from the centrifuge and re-insert it into a reader. Because this operation must be performed within a limited time interval following centrifugation, it requires the close attendance of the technician, which is inefficient and further exposes the technician to a potentially hazardous sample. This problem is particularly important in that relatively unskilled technicians may not appreciate the need for timely reading of the sample tubes, and thus may result in erroneous readings. Another problem which arises with the aforesaid prior art method results from the fact that the capillary tube expands slightly as a result of the high pressure of the blood sample column during centrifugation of the blood sample. After the cell layers have been compacted around the float, they form a relatively solid plug in the bore of the tube and, as the centrifuge decelerates, the wall of the tube springs back to its normal shape, and thus tends to "pumps" the blood cell layers upwardly in the tube. This action causes disruption of at least a part of the cell layers in some samples and thus renders such cell layers difficult or impossible to read.

It would be desirable to be able to measure the blood constituent layers while the tube Is still under centrifugal stress so that the cell layers are not disrupted, and also to reduce the amount of sample tube handling and the potential for error.

DISCLOSURE OF THE INVENTION

This invention relates to an assembly for quickly determining individual material volume measurements during centrifugation of a gravimetrically separable material mixture sample, such as an anticoagulated whole blood sample. Additionally, this invention relates to a method which can determine blood constituent volume measurements, and blood constituent counts during centrifugation. The method of this invention utilizes a combined centrifuge and reader which will perform the functions of both centrifugation and reading, and thus simplify the performance of the material layer measurements described in the aforesaid U.S. patents. By following the principles of this invention, white blood cell and platelet layers can be quantified with a minimum of sample manipulation and with minimal disruption of the formed layers in the blood sample.

The method of this invention involves the use of: a centrifuge; a high intensity fluorescent colorant excitation light source; a photodetector; and a processor controller for controlling operation of the assembly. The light source is preferably a high intensity pulsed light source which periodically illuminates the blood sample in the sampling tube as the latter is being centrifuged. Illumination of the blood sample in the tube causes fluorescence of certain of the blood cell constituents as well as illumination of the red blood cell layer, so that the photodetector can discriminate between the various cell layers in the tube that are gravimetrically compacted during the centrifugation step. Appropriate selection of filters on both the light source and the detector allows fluorescent light emanating from the fluorescing cell layers to be detected and measured, and also allows light reflected from material layers in the sample to be detected and measured. The pulsing of the light source is synchronized with the rotational position of the tube during centrifugation so that the tube will be momentarily illuminated as it passes by the photodetector. The optics and filters used in performing the method of this invention are generally similar to those described in U.S. Pat. No. 4,558,947, granted Dec. 17, 1985 to S. C. Wardlaw, the disclosure of which is incorporated herein in its entirety.

The light source for Illuminating the tube for the excitation of fluorescence must have sufficient emission in the excitation band (about 420–480 nm) to provide adequate emission energy from the sample tube, when received by a filtered, solid-state image dissector, such as a CCD array. Further, the energy must be delivered in the time period when the tube to be imaged is within the focal range of the detector, which is typically about 50 $\mu$sec. These requirements are best met by a xenon flash tube having an associated focusing means, rather than a diffuser, which flash tube is driven by a power supply capable of delivering short pulses at the needed power levels and wherein the light flashes are precisely tuned to the position of the tube relative to the detector when the flash tube is triggered.

The processor controller controls operation of the assembly in that, on command, it will: initiate centrifugation; monitor the RPM of the centrifuge; time the period of centrifugation; synchronize the light pulses with the ongoing centrifuge RPM; control operation of the photodetector; receive and store constituent layer readings; calculate the constituent layer compaction, and the resultant constituent counts or values; and shut the centrifuge down. The operator thus need only place the blood sampling tube in the centrifuge, and initiate operation of the assembly. For operator convenience and safety, the blood sampling tube can be contained in a special cassette of the general type described in U.S. Pat. No. 5,776,078, granted Jul. 7, 1998.

This invention also involves the use of a centrifuge component which is operable to synchronize the pulsing of a light source irregardless of the speed of rotation of the centrifuge. The inclusion of such a synchronization component in the centrifuge takes into account centrifuge wear, eliminates the need to set or adjust the pulsing synchronization of the assembly, and also allows the centrifuge to be intentionally operated at different speeds.

It is therefore an object of this invention to provide a method for obtaining information from a material mixture which will allow the reading of material layer thicknesses following a fixed period of centrifugation while the sample is still within the centrifuge and the centrifuge is still rotating.

It is a further object of this invention to provide a method of the character described wherein the material mixture is a sample of anticoagulated whole blood.

It is another object of this invention to provide a method of the character described wherein the ultimate thickness of a plurality of material layers in the sample being centrifuged can be derived from layer thickness measurements made during centrifugation.

These and other objects and advantages of the invention will become more readily apparent from the following detailed description of the invention when taken in conjunction with the accompanying drawings, in which:

DETAILED EXAMPLE FOR CARRYING OUT THE INVENTION

Figure 1:
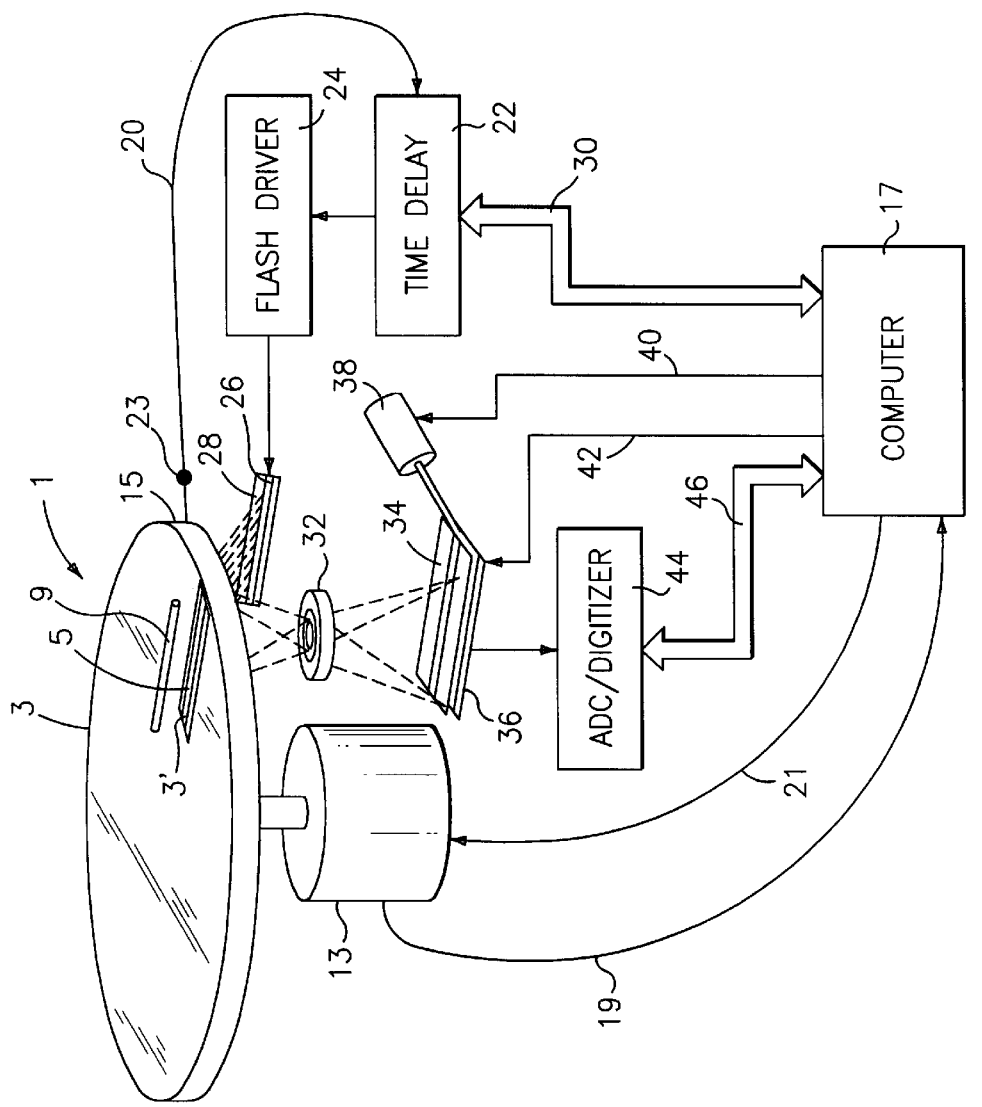
FIG. 1 is a schematic perspective view of a blood sample measurement assembly used in performing the method of this invention.

Referring now to FIG. 1, there is shown a schematic view of a combined centrifuge and reader assembly, which is indicated generally by the numeral 1. The assembly 1 includes a centrifuge platen 3 which includes a recess 5 for holding a transparent capillary tube 9. The tube 9 may be placed directly in the recess 5, or the capillary tube 9 may be held in a cassette (not shown) of the type disclosed in U.S. Pat. No. 5,776,078. In any event, at least one surface of the tube 9 must be optically visualized for the purpose of collecting the desired optical information from the tube contents. The centrifuge platen 3 is rotationally driven by a motor 13, which is controlled by output line 21 from an assembly controller 17. The rotational speed of the motor 13 is monitored by the controller 17 via line 19 thereby allowing the controller 17 to regulate the speed of the motor 13 and thus the centrifuge platen 3. When the centrifuge platen 3 reaches its predetermined operating speed, which may be between about 8,000 and about 12,000 RPM, the action of the controller 17 will depend upon the type of analysis required. When reading the material layer compaction following a fixed period of centrifugation, the controller 17 will energize the motor 13 for a desired fixed period of time and the layer compaction reading will be taken thereafter while the centrifuge continues to spin. As the platen 3 rotates, an indexing device 15 on the side of the platen 3 passes by and interacts with a sensor 23 which sends a signal through line 20 to a programmable delay 22. The indexing device 15 can be a permanent magnet and the sensor 23 can be a Hall-effect sensor. Alternatively, the indexing device 15 could be a reflective member on the edge of the platen 3, and the sensor 23 could be an infrared emitter-receiver pair. Still another alternative sensing device could include a sensor in the driving motor 13 provided that the platen 3 were rigidly affixed to the shaft of the driving motor 13.

After a predetermined time has elapsed from the receipt by the controller 17 of a signal from the proximity sensor 23, a flash driver 24 triggers a flash tube 26 that delivers a brief pulse of high intensity light, which pulse is preferably less than about fifty microseconds in duration. A filter and lens assembly 28 focuses the light of the desired wavelength, preferably between four hundred twenty and four hundred eighty nm, from the flash tube 26 onto the tube 9. When the flash tube 26 is positioned beneath the platen 3, the latter will include an opening 3' between the sample tube 9 and the flash tube 26 and filter and lens assembly 26. Due to the fact that the exact rotational speed of the platen 3 is monitored by the controller 17 via line 19, and since the circumferential distance between the position of the indexer 15 and the position of the tube 9 is fixed, the required time delay for timely energizing the flash tube 26 can be determined by the controller 17 and expressed through data bus 30 so as to control operation of the flash driver 24. The flash tube 26 is a high intensity light source, and may be a xenon or argon light source, for example.

When the tube 9 is illuminated by the flash tube 26, the light reflected by the cell layers, or light from fluorescence of the cell layers, is focused by a lens assembly 32 through a light filter set 34 onto a linear image dissector 36, which is preferably a charge-coupled device (CCD) having at least 256 elements and preferably 5,000 elements so as to achieve optimum optical resolution. Light of an appropriate wave length can be selected by an actuator 38 such as a solenoid or stepping motor which is controlled by the controller 17 via line 40 whereby the actuator 38 can provide the appropriate filter from the filter set 34, depending upon the light wavelength selected by the controller 17. Alternatively, electrically variable filters could be used to provide the proper light wavelengths, or CCDs with multiple sensors, each with its own particular filter could be used. Suitable electrically variable filters can be obtained from Cambridge Research and Instrumentation, Inc. of Cambridge, Mass. Suitable CCD's are available from Sony, Hitachi and others, and are common instrumentation components. In analyzing the fluorescing cell layers, light in two different fluorescent light wavelengths are collected, one green set of data in the wavelength range of about 530 to 560 nm; and a red set of data in the wavelength range of about 620 to about 680 nm. The filtered images are imaged on the image dissector 36 whose output is used to calculate the size and content of the cell sub-population bands.

Just prior to receiving the light flash from the flash tube 26, the electronic shutter in the CCD 36 is opened by the controller 17, via line 42. Immediately following the flash, the data from the CCD 36 is read into a digitizer 44 which converts the analog signals from each of the CCD cells into a digital signal. The digitized data is then transferred to the controller 17 through a data bus 46 so that the data can be immediately analyzed or stored for future examination in the controller 17.

Figure 2:
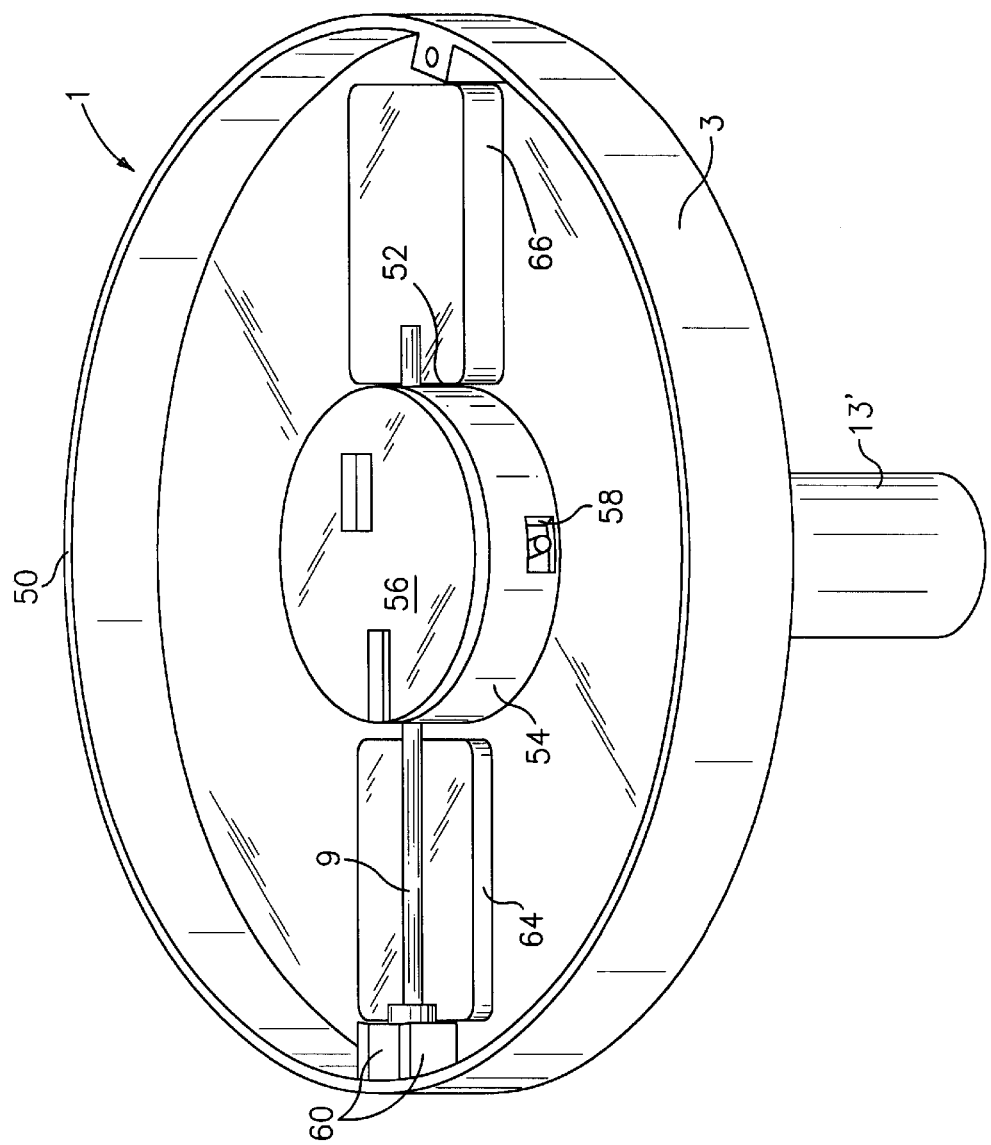
FIG. 2 is a perspective view of a preferred embodiment of a centrifuge platen and drive mechanism designed for use in connection with this invention.

Referring now to FIG. 2, there is shown a preferred embodiment of a centrifuge platen assembly 3 which is designed for use when the flashing light source 26 and the digitizer 44, which are shown in FIG. 1, are positioned above or below the platen 3. The platen 3 is generally dish-shaped and includes an outer rim 50 and a basal floor 52. A central hub 54 is secured to the platen floor 52, and the hub 54 is closed by a cover 56. The hub 54 has a pair of diametrically opposed windows 58 formed therein. The sample tube 9 is mounted on the platen 3. One end of the tube 9 is inserted into an opening in the hub 54, and the other end of the tube 9 is lowered into a slot 60 formed in a block 62 that is mounted on the platen rim 50. The platen floor 52 is provided with an opening (not shown) covered by transparent plate 64. A counterweight 66 is diametrically disposed opposite the plate 64 so as to dynamically balance the platen 3. The plate 64 allows the platen 3 to be used with light sources and detectors which are located either above or below the platen floor 52. They also allow the assembly 1 to utilize either reflected light, fluorescent emission or transmitted light in connection with the sample to achieve the desired results. The specific example shown in FIGS. 1 and 2 uses a single tube; however, multiple tubes can also be analyzed by the assembly 1 by mounting a sample tube in a diametrically opposed position on the platen 3, and by altering the timing from the index to the flash so as to provide readings for each separate tube. The drive shaft of the earlier described centrifuge motor 13 is designated by the numeral 13'.

Figure 3:
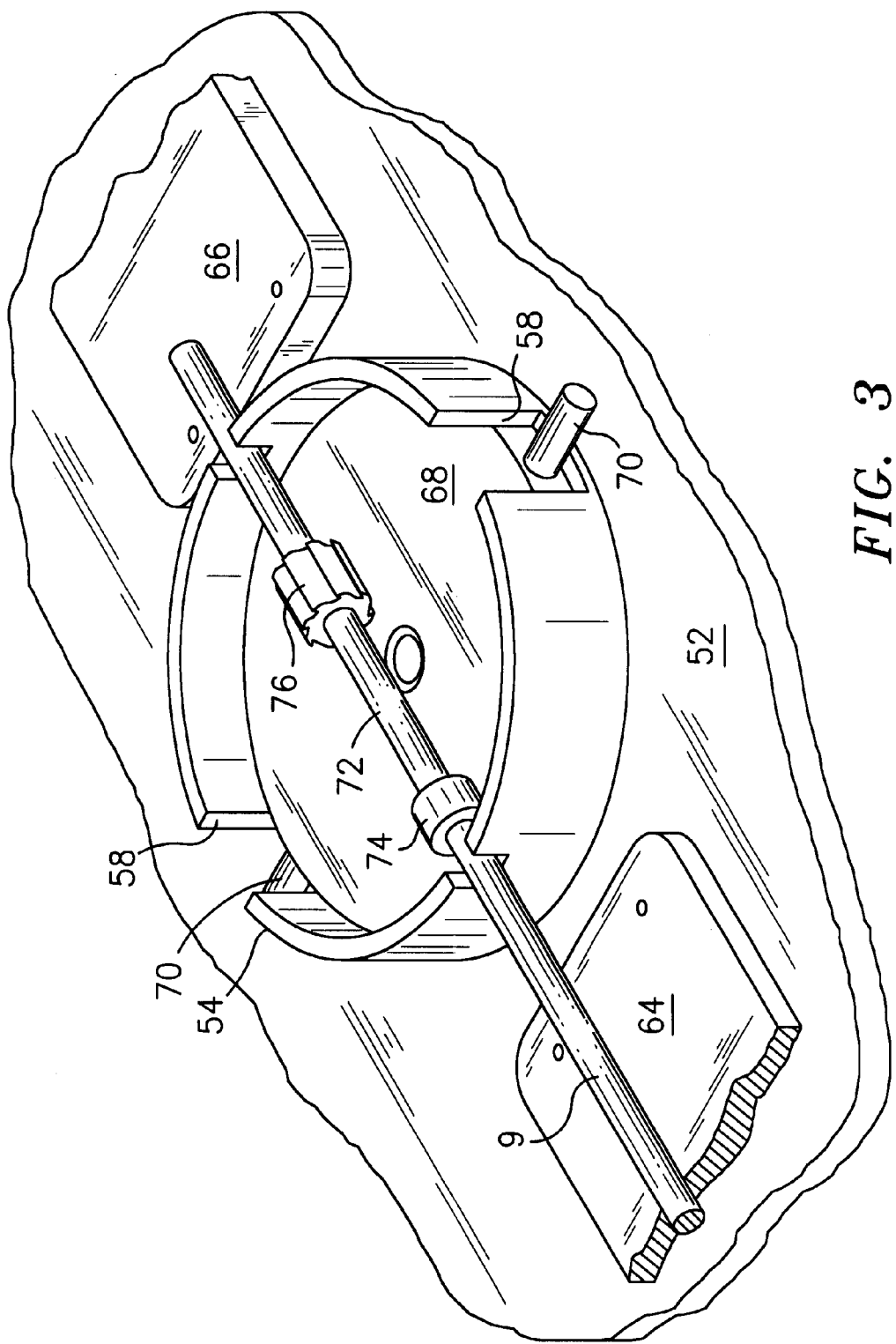
FIG. 3 is a fragmented perspective view of a tube holder and tube rotating mechanisms which are utilized in performing the method of this invention.
Figure 4:
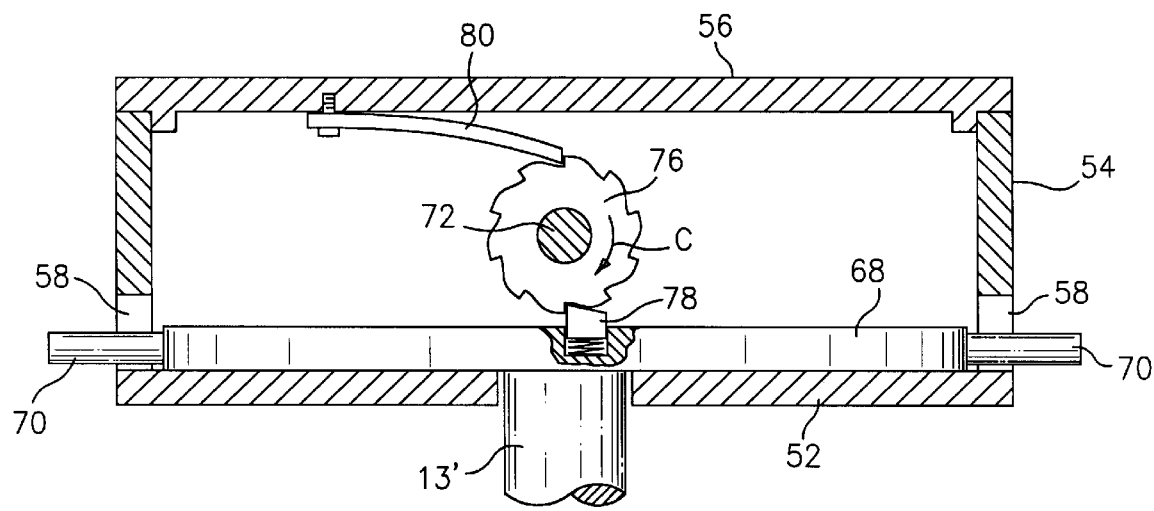
FIG. 4 is a sectional view of the tube rotating mechanism used in performing the method of this invention.

FIGS. 3 and 4 provide details of the manner in which the motor drive shaft 13' is connected to the platen 3; and also details of the manner in which the sample tube 9 is connected to the platen hub 54. The motor drive shaft 13' is affixed to a drive disc 68 which is disposed inside of the hub 54. The disc 68 has a pair of drive pins 70 secured thereto, which drive pins 70 project through the hub windows 58. The drive pins 70 provide the sole driving contact between the motor drive shaft 13' and the platen 3. Rotation of the disc 68 by the motor drive shaft 13' causes the pins 70 to engage the sides of the hub windows 58 thereby causing the hub 54 and the platen 3 to rotate with the disc 68. A rod 72 is rotatably mounted in the hub 54. The rod 72 includes a collar 74 at an end thereof which collar 74 receives one end of the sample tube 9. The collar 74 houses a resilient O-ring (not shown) which grips the end of the tube 9. A toothed ratchet 76 is mounted on the rod 72 and is operable to cause step-wise selective rotation of the collar 74 and sample tube 9 in the following manner. A spring-biased ratchet-engaging pawl 78 is mounted on the disc 68, and a ratchet-engaging blade spring 80 is mounted on the hub cover 56. When the centrifuge motor drive shaft 13' is being powered by the motor 13, rotation of the disc 68 moves the pawl 78 into engagement with one of the teeth on the ratchet 76 and the blade spring 80 moves down into engagement with a diametrically opposed tooth on the ratchet 76, as shown in FIG. 4. In order to selectively rotate the ratchet 76 and sample tube 9, power to the centrifuge motor 13 is periodically interrupted so as to momentarily slow rotation of the drive shaft 13'. The momentum of the platen 3 causes it, and its hub 54, to momentarily rotate at a faster rate than the disc 68 so as to disengage the pawl 78 from the ratchet 76 and to disengage the drive pins 70 from the platen hub 54. During this momentary disengagement, the pawl 78 will disengage from the ratchet tooth, and move to a position wherein it engages the next adjacent ratchet tooth. The motor 13 is then re-energized to full speed, causing the drive pins 70 to re-engage the hub 54 and causing the pawl 78 to impart a clockwise rotation step of the ratchet 76 and the sample tube 9. When the pawl 78 thus drives the next adjacent ratchet tooth, rotation of the ratchet 76 will cause the spring 80 to engage a diametrically opposed next adjacent tooth on the ratchet 76 thus stabilizing the ratchet 76 and the sample tube 9 in the new rotational position. Stepwise rotation of the sample tube 9 thus allows the image dissector 36 to "see" the entire periphery of the sample in the tube 9 as the latter is being centrifuged. Circumferential variations in the position of the descending sample component interfaces 8 will thus be taken into account by the system. The aforesaid pawl and ratchet tube rotating mechanism is the invention of Michael R. Walters of Becton Dickinson and Company, and is described in this application for the purpose of satisfying the "best mode" requirements of the patent statute.

Figure 5:
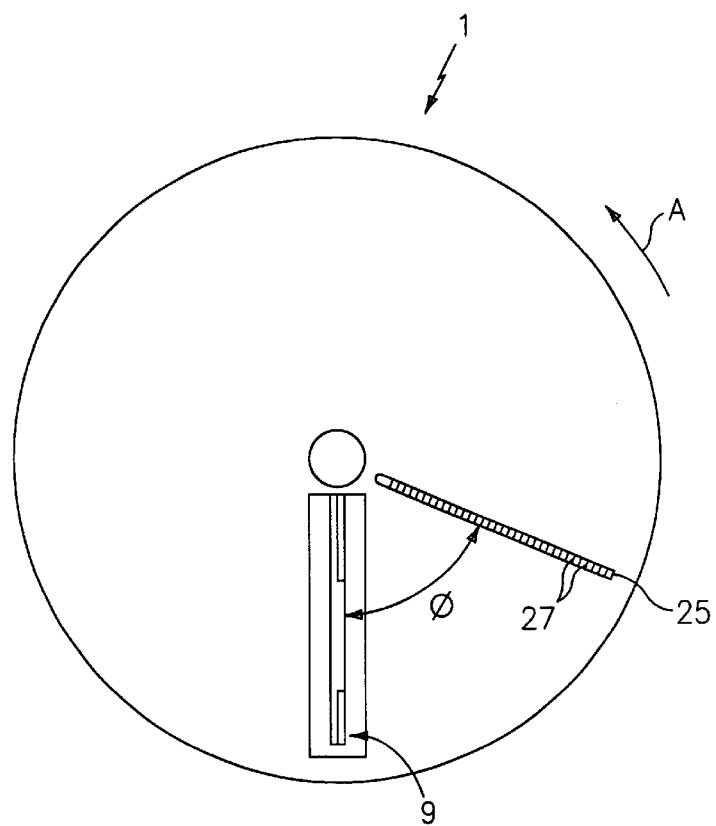
FIG. 5 is a plan view of the centrifuge platen showing a light pulse synchronization component of the platen assembly.

FIG. 5 is a plan view of the centrifuge platen 1 showing the sample tube 9 and a detectable target reference device 25 which is disposed on the platen 1 and angularly offset from the tube 9 by a precisely known angle $\phi$. The device 25 is preferably formed from a material such as a fluorescent plastic film which will fluoresce or reflect light in a manner similar to that of the tube 9. The device 25 preferably has a plurality of lines or bands 27 which are perpendicular to the axis of the device 25. The device 25 is preferably formed from a stable fluorescent or reflective fluorescent plastic film material so that the energy emitted from the device 25 can be used to calibrate the optical system of the instrument.

It is well known that quantitative measurements of fluorescent energy are difficult, in that the energy measured depends on the intensity of the excitation source, the temperature of the sample, and the responsiveness of the detection system, all of which may vary due to a number of factors. Although it is very difficult to provide any type of long term calibration, it is practical to periodically compare the energy level response from a target such as the reference device 25, which response is stable over time, to the energy level response from the sample 9, which response may not be stable over time. When the energy level response from the sample 9 appears to the instrument to be low, a comparison of successive sample 9 energy level responses and reference device 25 energy level responses can be made. The comparison of energy level responses can be used to determine whether the sample 9 energy level response is low because of a characteristic of the sample 9, or because of a system error in the instrument's fluorescence response measurement system. If the latter cause of faulty signal level measurements is detected, then the instrument's signal level measurement system will be recalibrated based on the known signal level measurements received from the reference device 25.

Furthermore, the length of the bands 27 in the reference device 25 can be sensed by the imaging system in the instrument, and since the length of the bands 27 can be precisely delineated, they can be used for spatial calibration of the entire imaging system. One optical error which might occur, for example, is that the imaging lens and filter system may project an image onto the detector 36 which is non-linear. Thus, equidistant spatial points at the center of the image may not cover the same detector area as those points at the edge of the image. This phenomenon is encountered in photography wherein it is referred to as a "pincushion" or "barrel" effect, and it prevents accurate spatial measurements unless it is remedied. If the equidistant bands 27 are mapped by the detector 36 across the entire image length, then any distortion can be detected and compensated for in the final calculations.

In use, the centrifuge platen 1 is rotated in the direction indicated by the arrow A until it reaches operating speed. The pulsing of the flash tube 26 is adjusted by the microprocessor 17 until a clear image of the target device 25 is obtained by the image dissector 36. In practice, the speed of the centrifuge is first calculated by using the timing pulses given by the sensor 23. From this data, an assumed delay time from the sensor pulse to the flash trigger is calculated based upon either previously obtained times or a time which is preprogrammed into the instrument when the instrument is assembled. Then a series of images of the target device 25 is captured at that "starting time" and at other starting times which are both shorter and longer. The flash time delay which gives the best response from the device 25 is then chosen and implanted into the system's operating software.

At this point, inasmuch as both the platen speed and the angle ø between the target device 25 and the tube 9 are known, the time delay between the device 25 and the detector 36 can be calculated, and the calculated time delay value is added to the time delay from the timing pulser to the detector 25, so as to provide a total time delay to be programmed into the delay 22 for pulsing the flash tube 26 so as to precisely illuminate the sample tube 9.

It will be appreciated that the aforesaid system and method of operation will suffice to synchronize the flash tube illumination pulses with the passage of the sample tube past the flash tube at any centrifuge platen rotational speed. The aforesaid procedure will have utility, irregardless of aging of centrifuge components, system or sample operating temperatures, or similar operating condition variations.

Since many changes and variations of the disclosed embodiment of the invention may be made without departing from the inventive concept, it is not intended to limit the invention otherwise than as required by the appended claims.

What is claimed is:

1. A method for determining the amount of a target component in an anticoagulated whole blood sample, which blood sample is contained in a transparent tube along with a fluorescent dye which can cause the target component in the blood sample to fluoresce, said method comprising:
   a) the step of placing the tube on a centrifuge platen;
   b) the step of spinning the platen so as to commence gravimetric compaction of the target component into a discernable layer in the tube;
   c) the step of periodically exposing the blood sample to a pulsed high intensity light beam which is in a wavelength range of between about 420 to about 480 nm so as to cause said target component in the blood sample to emit a fluorescent signal while the tube is being centrifuged on the platen;
   d) the step of collecting fluorescent light data emitted from said target component which light data is in a first wavelength range of between about 530 and about 560 nm, and which is within a second wavelength range of between about 620 and about 680 nm while the tube is being centrifuged on the platen;
   e) the step of converting said collected data into a target component layer thickness reading; and
   f) the step of converting said recorded layer thickness reading into a quantification of the amount of the target component in the blood sample.

2. A system for determining the extent of compaction of a target constituent component layer in a centrifuged sample of anticoagulated whole blood which sample is contained in a transparent tube, said system comprising:
   a) a centrifuge assembly comprising a platen and a motor for rotating the platen, said platen including a support for the tube during centrifugation of the blood sample;
   b) a high intensity light source for illuminating the tube during centrifugation of the tube on said platen;
   c) a first filter interposed between the light source and the tube for converting light emitted from said light source to a wavelength which is in the range of between about 420 to about 480 nm;
   d) a linear image dissector operatively associated with said centrifuge platen so as to create analog signals resulting from light rays emitted from the sample in the tube, said analog signals being representative of signal values from a plurality of points along the tube, which when digitized, allow a microprocessor to locate and measure the distance between adjacent interfaces of the target component layer;
   e) a second filter set interposed between the image dissector and the tube for converting light rays emitted from said sample and transmitted to said image dissector to a first wavelength which is in the range of between about 530 to about 560 nm, and to a second wavelength which is in the range of between about 620 and about 680 nm;
   f) a digitizer connected to said image dissector for converting said analog signals to digital signals;
   g) a microprocessor connected to said digitizer for receiving said digital signals from said digitizer, said microprocessor being operable to convert said digital signals into a quantification of the degree of compaction of said target constituent component layer, and thereby the volume of said target constituent component layer; and
   h) a mechanism for periodically pulsing said light source so that the latter is activated only when the sample tube passes by said image dissector.

* * * * *